Figure 1:
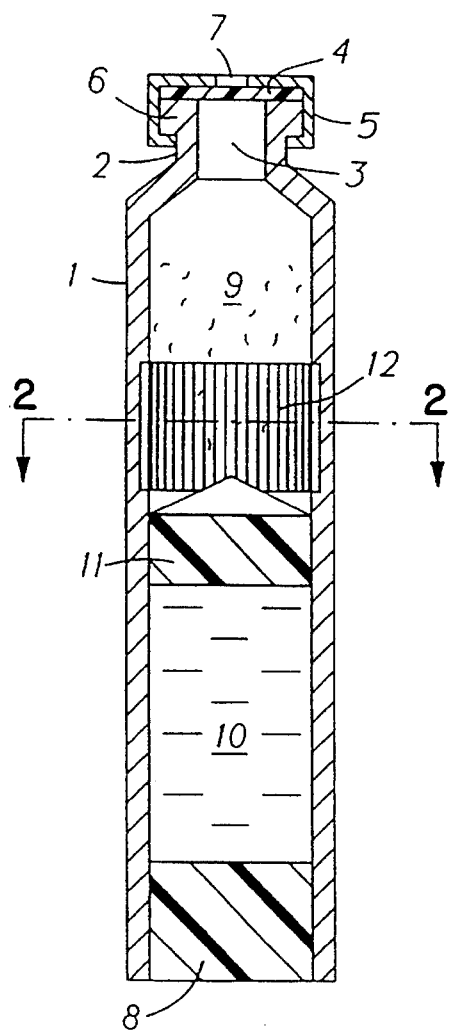

United States Patent [19]

Hjertman et al.

[11] Patent Number: 5,501,673
[45] Date of Patent: Mar. 26, 1996

[54] INJECTION CARTRIDGE

[75] Inventors: Birger Hjertman, Vällingby; Gustav Levander, Bromma; Olle Ljunquist, Täby, all of Sweden

[73] Assignee: Pharmacia AB, Stockholm, Sweden

[21] Appl. No.: 325,209

[22] PCT Filed: Apr. 16, 1993

[86] PCT No.: PCT/SE93/00337

§ 371 Date: Dec. 8, 1994

§ 102(e) Date: Dec. 8, 1994

[87] PCT Pub. No.: WO93/20868

PCT Pub. Date: Oct. 28, 1993

[30] Foreign Application Priority Data

Apr. 21, 1992 [SE] Sweden ................... 9201248

[51] Int. Cl.⁶ .................................................. A61M 5/00
[52] U.S. Cl. ......................... 604/191; 604/416; 34/296

[58] Field of Search .................. 604/191, 416, 604/82, 89–91, 224, 232, 234, 208, 211; 34/296–297

[56] References Cited

U.S. PATENT DOCUMENTS

| | | |
|---|---|---|
| 2,591,046 | 4/1952 | Brown . |
| 4,968,299 | 11/1990 | Ahlstrand et al. . |
| 5,380,087 | 1/1995 | Haber et al. . |
| 5,385,545 | 1/1995 | Kriesel et al. . |
| 5,435,076 | 7/1995 | Hjertman et al. . |

*Primary Examiner*—C. Fred Rosenbaum
*Assistant Examiner*—Perry E. Van Over
*Attorney, Agent, or Firm*—Pollock, Vande Sande & Priddy

[57] ABSTRACT

An injection cartridge of the dual-chamber type has a bypass connection between its two chambers which is arranged such that the interior wall of the cartridge is modified in a determined area in such a way that the movable wall between the two chambers does not seal completely against the interior wall in said area.

20 Claims, 4 Drawing Sheets

INJECTION CARTRIDGE

The present invention refers to an injection cartridge of the dual-chamber type. In more detail, the invention refers to an injection cartridge of the dual-chamber type which has an improved arrangement of bypass means for the liquid component.

Injection cartridges of the dual-chamber type are well-known and have found a wide use. Such cartridges are primarily intended to be used when the liquid pharmaceutical composition to be injected is not stable for any extended period of time. In such cases, the composition to be injected is provided as two separate components, one solid component comprising the active pharmaceutical component in a dry state, and one liquid component comprising a solvent or dispersing agent for the solid component. These two components are enclosed in an injection cartridge of the dual-chamber type, such that the solid component is usually enclosed in a front chamber, while the liquid component is enclosed in a rear chamber. (In the following specification and claims, the expressions "front" and "rear" are to be regarded in relation to the direction in which the injectable composition is transported when an injection is administered.)

The two components are separated by a movable wall which seals against the interior wall of the cartridge. The rear chamber, which contains the liquid component, is also closed at its rear end by a piston which seals against the interior wall of the cartridge.

At its front end, the cartridge is usually closed by a rubber septum which is held into place by a metal capsule. This metal capsule has a central opening which exposes the rubber septum. Through this opening, a hollow needle may be inserted through this the septum to give a connection with the interior of the cartridge.

For conducting the liquid component over to the solid component for dissolution or dispersion, conventional dual-chamber injection cartridges are provided with at least one bypass channel in the wall of the cartridge. When the movable wall which separates the two chambers is at a suitable position, the bypass channel is exposed, so that the liquid component may flow around said movable wall and be mixed with the solid component.

When the cartridge is to be readied for the administering of one or more injections, pressure is applied to the rear piston to urge it forward. This pressure will be transmitted through the liquid phase, which is largely incompressible, so that also the movable wall, which separates the two chambers, is urged forward. When front movable wall has been moved forward a determined length, it will be situated at the bypass channel, such that a flow of liquid from the rear chamber to the front chamber becomes possible. Further forward movement of the rear piston will now push the liquid from the rear chamber into the front chamber, while the movable wall remains essentially stationary.

When all the liquid has been expelled from the rear chamber, the rear piston will abut the movable wall, and further pressure forward will move the two walls together, to act like a single piston. The rubber septum closing the front end of the cartridge should now have been pierced by a hollow needle, which makes it possible to expel the ready-mixed preparation from the front chamber to be administered to a patient.

The dual-chamber injection cartridges described above have a number of important advantages and have found a wide use. One important use is in injection devices which are intended to be used by the patient to administer injections to himself. It is easy for the patient to prepare the injectable preparation from the two components immediately before the administering, and the risk of contamination is greatly reduced.

However, the conventional injection cartridges of the dual-chamber type also have certain shortcomings. The cartridges are often used in injection devices which more or less have the appearance of a fountain pen, and it is desirable that such a device should not be unduly thick or long. Thus, any measure which may make such a device slimmer and/or shorter is highly desirable.

The bypass channel in the wall of conventional cartridges creates a longitudinal ridge in the outer wall of the cartridge, and makes it necessary to use an injection device having an undesirably thick barrel to make room for the cartridge. Furthermore, it is desirable to make the forward movement of the movable wall as short as possible, as this makes it possible to use an injection device having a shorter barrel.

The desirable improvements mentioned above are obtained by the present invention. According to the invention, an injection cartridge of the dual-chamber type is provided, which comprises a tubular barrel which at its front end is sealed by a closure which may be penetrated by an outlet conduit for a liquid preparation from the cartridge, at its rear end is closed by a piston which may be moved forward, and which comprises a movable transversal wall inside the barrel, said movable wall dividing the cartridge into two separate chambers, and a bypass connection between the two chambers, said connection being openable by the displacement of said movable wall to permit a bypass flow of a liquid between the chambers. What characterizes the invention is that said connection between the two chambers is arranged as a modification of the interior wall of said barrel along a determined area, such that said movable wall does not seal completely against the interior wall of the barrel within said area.

In a preferred embodiment of the invention, said modified area extends completely around the circumference of the interior wall of the cartridge, such that a flow of liquid is permitted around the complete circumference of the movable wall.

In another preferred embodiment, the modification of the interior wall of the cartridge is arranged as a plurality of lands and grooves in said interior wall, said lands and grooves preferably having an axial direction. In a still more preferred version of this embodiment, the lands extend inward from the interior wall of the cartridge, such that the interior diameter between the lands is smaller than the nominal interior diameter of the cartridge.

In a further preferred embodiment of the invention, said axial lands and grooves are interrupted by essentially peripheral grooves having essentially the same depth as said axial grooves.

In a still further preferred embodiment, the modified area of the interior wall of the cartridge is divided into at least two circumferential areas, which have the same spacing as the distance between the same number of circumferential sealing ridges on the movable wall.

The depth of said grooves and the height of said lands is preferably between 0.06 and 0.6 mm from the interior wall of the cartridge.

Thus, the basic inventive idea is that the dual-chamber cartridge no longer contains a bypass channel, but a bypass area of modifications of the interior wall. Such an area affords a great number of shallow channels, which have at least the same flow capacity as one large channel. However, because of the shallow depth of the modifications, no exterior ridge or increased thickness of the cartridge wall will be necessary, and this makes it possible to use an injection device having a slimmer barrel.

The invention will now be described in closer detail, with reference to the enclosed drawings.

Figure 3:
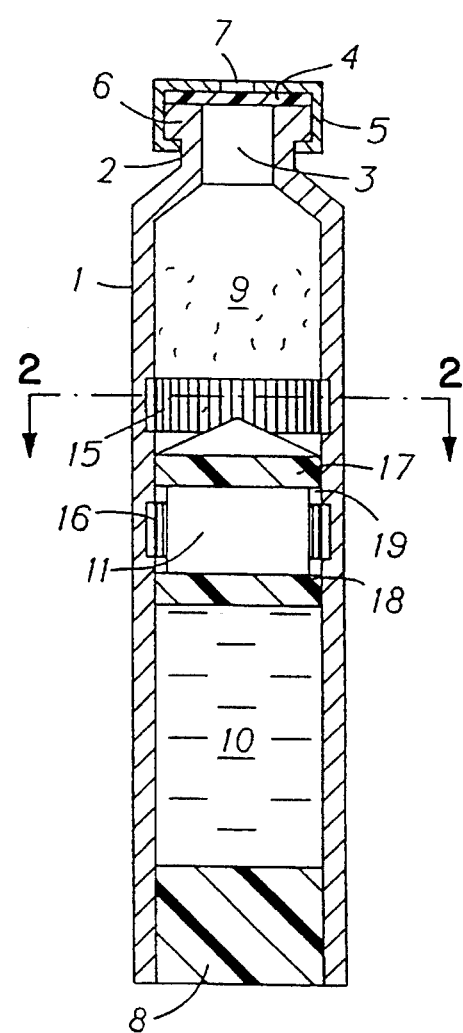
Figure 2:
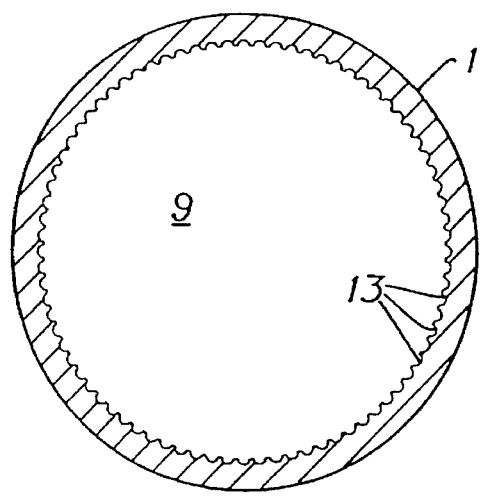
Figure 4:
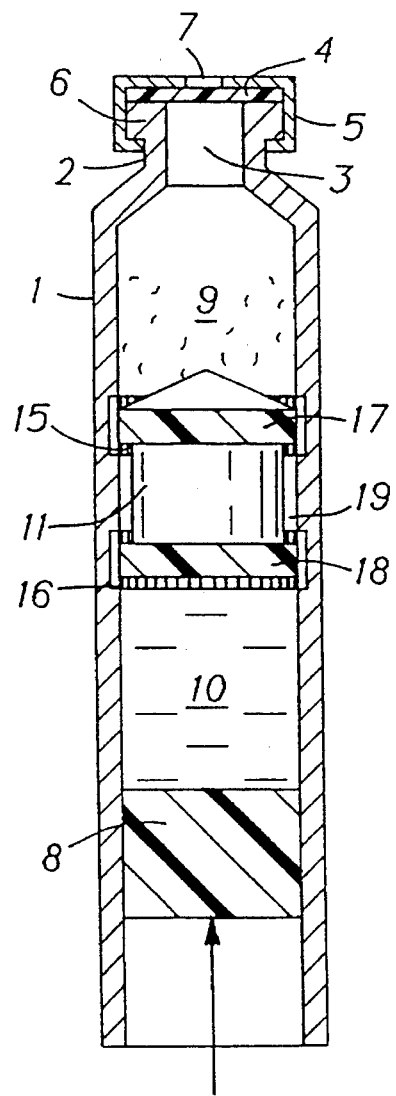
Figure 5:
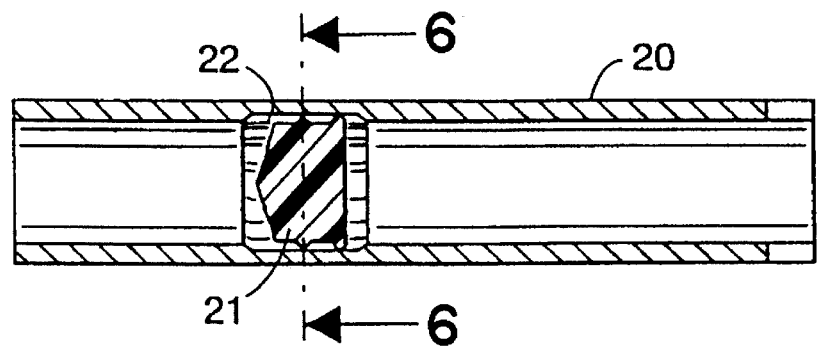
Figure 6:
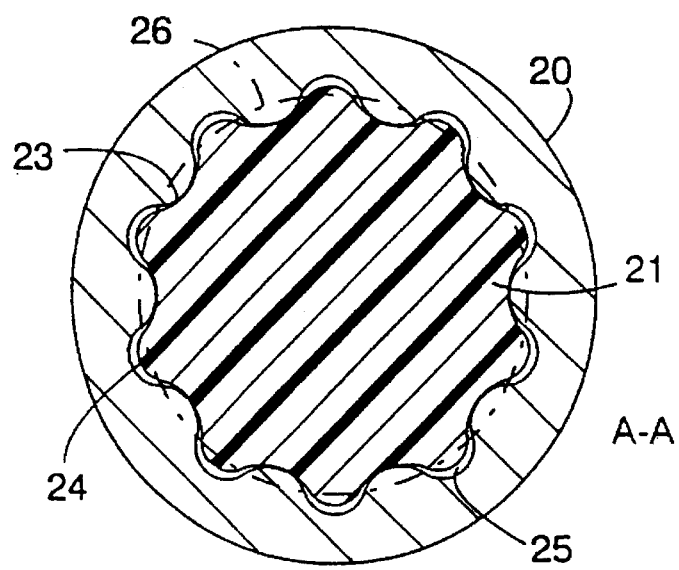
Figure 7:
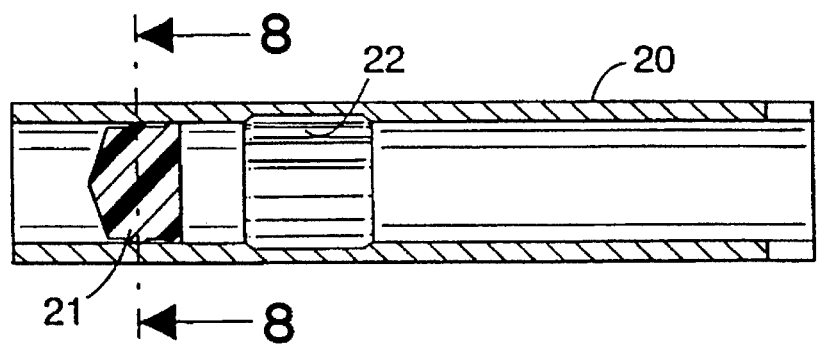
Figure 8:
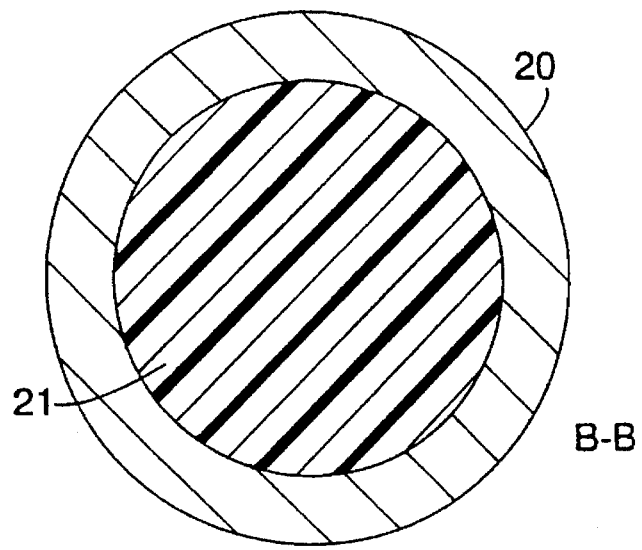

In the drawings, FIG. 1 shows a dual-chamber injection cartridge according to the invention. FIG. 2 shows a sectional view of such a cartridge. FIG. 3 shows another embodiment of a dual-chamber injection cartridge of the invention, and FIG. 4 shows the same cartridge in the stage when the two components are mixed. FIG. 5 shows a preferred embodiment of an injection cartridge of the invention, and FIG. 6 shows a transverse sectional view of the same cartridge at the position of the piston. FIG. 7 shows the same embodiment of the cartridge with the piston displaced from the bypass zone, and FIG. 8 shows a sectional view of the same cartridge at this position of the piston. In the figures of the drawing, like parts have the same reference numbers. Furthermore, some of the details in the drawing are shown in an exaggerated scale for clarity.

FIG. 1 shows a dual-chamber injection cartridge having a cylindrical barrel 1 and a neck portion 2 at its forward opening 3. This opening is closed by a septum 4 of rubber or some similar material which has sealing properties, and the septum is held in place by a metal capsule 5, which is fastened around a flange 6 at the forward end of the neck portion 2. The capsule 5 has a central opening 7, where the septum is exposed and may be penetrated by a hollow needle when desired.

At its rear end, the barrel 1 of the cartridge is closed by a piston 8, which may be moved forward when the cartridge is to be readied for an injection.

The cartridge is divided into a front chamber 9, which usually contains the solid component of the injectable preparation, and a rear chamber 10, which usually contains the liquid component of said preparation, by means of the movable wall 11. In the position shown in the figure, the movable wall seals against the interior wall of the cartridge, and nothing can pass between the two chambers.

In front of the movable wall 11, the interior wall of the barrel 1 of the cartridge is provided with modifications 12, which cause that the movable wall 11 in this area does not seal completely against the interior wall. In the figures of the drawing, these modifications are shown as shallow grooves extending in the longitudinal direction of the barrel 1. This is shown more clearly in FIG. 2, which is a sectional view of the barrel 1 along the line 2—2 in FIG. 1.

In FIG. 2, it is shown how the barrel 1, which here encloses the front chamber 9, is provided with a plurality of shallow longitudinal grooves 13. For clarity, the depth of these grooves is exaggerated in the drawing. In the preferred embodiment shown, the shallow grooves are evenly distributed along the internal circumference of the barrel. However, it is also possible to have the grooves present in certain discrete areas only. What is important is that the grooves should together afford a passage that is sufficient for the flow of the liquid component from the rear chamber to the front chamber.

It is understood that the area of surface modifications should have such an extension in the axial direction that it is somewhat longer than the movable wall 11, to make it possible for a flow of liquid to bypass said movable wall.

It will also be seen that the grooves 13 can take up so much of the interior wall that the movable wall 11 is properly guided only by small ridges. This is usually not a problem.

The longitudinal grooves 13 may also be broken by a number of peripheral grooves around the interior circumference of the barrel 1. This may improve the flow of the liquid and will aid in removing air from the system.

Furthermore, it should be noted that it is not strictly necessary that the bypass area 12 is formed by grooves. Other modifications of the interior surface are also possible, such as various patterns of roughened surfaces, small projections, and the like. In a preferred embodiment, such projections are shaped as lands extending in the axial direction. The height of such projections should also preferably be between 0.06 and 0.6 mm. The important feature is that in said area 12, the movable wall 11 should not seal completely against the barrel, but permit a bypass flow of the liquid component between the chambers.

When the cartridge is to be readied for injection, a forward-directed pressure is applied to the piston 8 at the rear of the cartridge. This pressure is transmitted through the essentially incompressible liquid in the rear chamber 10 and acts on the movable wall 11 to urge it forward. When the movable wall has been moved forward so far that it is in the area of the modified internal surface of the barrel 1, it will no longer seal completely against the interior wall of the barrel, and it will be possible for the liquid component to flow from the rear chamber 10 into the front chamber 9, to be mixed with the solid component in this chamber. Further pressure on the rear piston 8 will expel all of the liquid from the rear chamber 10, until finally the rear piston will rest against the rear surface of the movable wall 11. At this stage, the movable wall 11 and the rear piston 8 will act together as one single piston.

Before the liquid component is made to flow over into the front chamber 9, the septum 4 closing the front chamber 9 will usually have been pierced with a hollow needle which is connected to a needle for administering the injection, or which itself serves as such an injection needle by means of its forward pointed end. This prevents the build-up of an excessive overpressure in the front chamber 9. After all of the liquid component has been made to flow over into the front chamber 9 and has been thoroughly mixed with the solid component, further pressure on the combined rear piston 8 and movable wall 11 will serve to expel the mixed injectable preparation through the hollow needle for administering to a patient.

Before the cartridge is readied for injection, it is placed in a suitable holder device. Such devices are known for carrying out the mixing of the two components and for subsequent administering of the injectable preparation. In many cases, they also comprise means for metering out predetermined amounts of the preparation to be injected. There are a number of such devices commercially available, which are arranged such that a patient may himself make the cartridge ready for injection, and administer the injections to himself by means of such a device.

FIGS. 3 and 4 show a preferred embodiment of the invention. The arrangements at the front and rear ends of the cartridge are the same here as shown in FIG. 1.

However, the area of modification of the internal wall of the barrel 1 is here divided into at least two areas 15 and 16. These areas are arranged as spaced bands 15 and 16, which each contain the same types of surface modifications as those mentioned in connection with FIGS. 1 and 2. A sectional view along the lines 2—2 in FIG. 3 will show exactly the same as FIG. 2 in connection with FIG. 1.

The movable wall 11 is composed of a central part having a smaller diameter than the interior diameter of the barrel 1, and at least two circumferential sealing ridges 17 and 18 at the front and rear end of the movable wall, respectively. This gives a space 19 defined by the two sealing ridges 17 and 18, the part of the movable wall having a smaller diameter, and the interior wall of the barrel 1.

The spacing between the two sealing ridges 17 and 18 is the same as the spacing between the two bands 15 and 16 of surface modifications of the interior wall. These bands also have a somewhat greater axial length than tile axial length of each of the sealing ridges 17 and 18, such that a flow of liquid around said sealing ridges becomes possible.

In the initial stage, before the cartridge has been readied for injection, the movable wall is in such a position inside the barrel 1 of the cartridge that the front sealing ridge 17 lies between the two bands of modification 15 and 16. The rear sealing ridge 18 should lie behind the rear band 16. In this way, a complete seal between the front and rear chambers is assured.

When the cartridge is to be readied for injection, pressure is applied on the rear piston 8, as described previously. This will bring about that the movable wall 11 is urged forward, until it is in the position shown in FIG. 4. It will be seen that the two sealing ridges are now positioned opposite the bands of modification 15 and 16, and a liquid flow is now possible from the rear chamber 10 around the rear sealing ridge 18, into the space 19, and around the front sealing ridge 17 into the front chamber 9.

The advantage of this embodiment is that the movable wall 11 will only have to be moved the short distance corresponding approximately to half the spacing between the two bands 15 and 16. This makes it possible to use a shorter cartridge and a shorter injection device for housing the cartridge. For injection devices which are to be carried around by the patient himself, this can be of considerable importance.

It is also possible to use more than two areas of surface modification and corresponding sealing ridges of the movable wall. This gives a more secure seal, but the construction becomes more complicated and therefore also more expensive.

In FIGS. 5 to 8 is shown an especially preferred embodiment of an injection cartridge according to the invention. In these figures, only the part of the cartridge around the bypass area and the front piston is shown, while the arrangements at the front and rear ends of the cartridge are the same as shown in the previous figures.

FIG. 5 shows the barrel of the cartridge 20 with the piston 21 positioned in the bypass area 22. FIG. 6 is a sectional view along 6—6 in FIG. 5 (in a larger scale for the sake of clearness) which shows the shape of the cartridge wall in the bypass area and of the piston therein. It will be seen that the interior wall of the cartridge 20 is provided with lands 23 and grooves 24, and that the piston 21 has been deformed to adapt to the lands 23 and grooves 24 in this bypass area. This adaption is not complete, however, and axial channels 25 are formed between the bottoms of the grooves 24 and the deformed piston 21. These channels 25 afford the bypass for the liquid from the rear chamber to the front chamber of the cartridge.

FIG. 7 shows the cartridge 20 after the piston 21 has been moved further forward of the bypass area 22, and FIG. 8 shows a sectional view (in a larger scale) along 8—8 in FIG. 7. It will be seen that the piston 21 has now adapted to the smooth interior wall of the cartridge 20 and completely seals against said interior wall.

It is important feature of the embodiment shown in FIGS. 5 to 8, especially then in FIG. 6, that the lands 23 extend inward from the nominal interior circumference of the cartridge 20, while the grooves 24 extent outward from said nominal circumference. The nominal interior circumference and interior diameter of the cartridge are defined as the interior circumference and interior diameter, respectively, of the smooth-walled portion of the cartridge and said circumference is symbolized by the dashed line 26 in FIG. 6. The height of the lands 23 and the depth of the grooves 24, as well as their number, should be correlated to each other such that the piston 21 has the same cross-sectional area when it is in the bypass part as when it is in the smooth-walled parts of the cartridge.

When the piston 21 is in the smooth-walled part of the cartridge, it has to be compressed to a certain extent to seal securely against the interior wall of the cartridge. This compression of the piston will make its length increase to some extent. The compression of the piston will also increase its resistance against movement in the axial direction. A suitable degree of resistance can be obtained by the selection of an appropriate degree of compression, as well as by a suitable treatment of the interior wall of the cartridge, such as siliconizing. A siliconizing treatment, however, may also cause contamination of the product in the cartridge.

When the piston 21 has been moved to the bypass area 22, parts of it will be further compressed by the lands 23 extending inwards from the nominal circumference 26, while other parts of it are allowed to expand into the grooves 24, without filling up said grooves completely. It is an important feature of this embodiment of the invention that this further compression and expansion should balance each other out, such that the cross-section area of the piston in the bypass part will be essentially the same as the cross-section area of the piston in the smooth-walled part of the cartridge. This will mean that the length of the piston 21 will be essentially unchanged, as a consequence of which the resistance against axial displacement of the piston will also be essentially unchanged. This is an important advantage, as the constant resistance contributes to an increased accuracy in the mixing and metering out of the product in the cartridge.

In the bypass areas of the prior art, the diameter is usually somewhat greater than in the smooth-walled parts of the cartridge. Thus, the resistance against axial displacement of the piston is less in the bypass area, and the change in resistance may be rather abrupt. This may cause a user pushing the piston forward to move the piston too fast in the bypass area, so that the piston will pass over the bypass area before all the liquid in the rear chamber has been transferred to the front chamber. The risk of this occurring is greater when the piston is moved forward by manual pressure instead of by the use of a screw mechanism.

Thus, the interaction between the piston and the interior wall of the cartridge in the bypass area is a critical feature for obtaining a correct and accurate mixing of the liquid and the solid components in the cartridge. Through this embodiment of the present invention, the risk of errors in the mixing process is greatly diminished.

The lands and grooves in the interior wall of the cartridge can be manufactured by a mechanical treatment of the interior wall while the cartridge barrel is in a softened state. Thus, the cartridge barrel, which is usually made of glass or a thermoplastic material, is heated to a suitable degree of softness, and a wheel having a circumferential shape corresponding to the profile desired for the interior wall is inserted into the barrel and is rolled around the circumference of the interior wall at the place of the bypass area. The wheel will then emboss the interior wall with the desired pattern. The wave form shown in FIG. 6 has turned out to be advantageous, but other shapes of the lands and grooves are also possible. The essential feature is that the dimensions of the lands and grooves should be such that the piston in its deformed state in the bypass part should have essentially the same cross-section area as in the smooth-walled portion of the cartridge barrel, while affording bypass channels in the bottoms of the grooves.

It goes without saying that the preferred embodiment shown in FIGS. 5 to 8 may be combined with the embodiment shown in FIGS. 3 and 4, where the modification of the interior wall in the bypass area is divided into at least two separate areas.

The injection cartridge of the invention is especially advantageous to use together with sensitive preparations, such as growth hormones and other proteins. Such preparations have to be reconstituted under very mild conditions, as there is otherwise a risk that they will be denatured. Through the present invention, a liquid flow around the whole circumference of the movable wall is arranged, and this makes possible a mixing of the two components under very mild conditions. This type of liquid flow also aids in removing trapped air from the composition.

The manufacture of the injection cartridges according to the present invention does not present any difficulties to a person skilled in the art. The modifications of certain areas of the interior wall may be carried out by the use of a suitable grinding tool, or as described in the foregoing for the preferred embodiment. In all other respects, the preparation and filling of the cartridges are carried out in the same way as for conventional injection cartridges of the dual-chamber type.

The injection cartridge of the invention may be manufactured from conventional materials, such as glass or suitable plastic materials. Such materials are well-known to those skilled in the art.

We claim:

1. An injection cartridge of the dual-chamber type, comprising a tubular barrel which at its front end is sealed by a closure which may be penetrated by an outlet conduit for a liquid preparation from the cartridge, and at its rear end is closed by a piston which may be moved forward, and a movable transversal wall inside said barrel, said movable wall dividing the cartridge into two separate chambers, and a bypass connection between the two chambers, said bypass connection being openable by the displacement of said movable wall to permit a bypass flow of liquid between the two chambers, and characterized in that said connection between the two chambers is arranged as a modification of the surface of the interior wall of the barrel, said modification extending completely around the circumference of the interior wall and comprising a plurality of lands and grooves in said interior wall surface, said lands extending inward from the nominal interior circumference of the barrel and said grooves extending outward from said nominal interior circumference, such that a liquid flow may be arranged around the whole circumference of the movable wall.

2. Injection cartridge according to claim 1, characterized in that the height of the lands and the depth of the grooves, as well as their number, are correlated in such a way that the movable transversal wall has essentially the same cross-sectional area when it is positioned in the area of said lands and grooves as when it is positioned in the smooth-walled part of the barrel.

3. Injection cartridge according to claim 1, characterized in that said modification consists of a pattern of a roughened surface or of small projections in said interior wall surface.

4. Injection cartridge according to claim 1, characterized in that said modified area of the interior wall surface is divided into at least two spaced circumferential areas, and that the movable wall is provided with the same number of peripheral sealing ridges, said ridges and said areas having the same spacing.

5. Injection cartridge according to claim 1, characterized in that the depth of said grooves and/or the height of said lands or projections is between 0.06 and 0.6 mm.

6. An injection cartridge according to claim 2, wherein said modification comprises a pattern of a roughened surface or of small projections in said interior wall surface.

7. An injection cartridge according to claim 2, wherein said modified area of said interior wall surface is divided into at least two spaced circumferential areas, and the movable wall is provided with the same number of peripheral sealing ridges, said ridges and said areas having the same spacing.

8. An injection cartridge according to claim 3, wherein said modified area of said interior wall surface is divided into at least two spaced circumferential areas, and the movable wall is provided with the same number of peripheral sealing ridges, said ridges and said areas having the same spacing.

9. An injection cartridge according to claim 2, wherein the depth of said grooves and/or the height of said lands or projections is between 0.06 and 0.6 mm.

10. An injection cartridge according to claim 3, wherein the depth of said grooves and/or the height of said lands or projections is between 0.06 and 0.6 mm.

11. An injection cartridge according to claim 4, wherein the depth of said grooves and/or the height of said lands or projections is between 0.06 and 0.6 mm.

12. An injection cartridge according to claim 1, wherein said modification of the interior wall surface of the barrel extends completely around the circumference of said interior wall.

13. An injection cartridge according to claim 1, where said modification of the interior wall surface is arranged as a plurality of lands and grooves in said interior wall.

14. An injection cartridge according to claim 13, wherein the lands extend inward from the nominal interior circumference of the tubular barrel, and the grooves extend outwardly from said nominal circumference.

15. An injection cartridge according to claim 14, wherein the height of the lands and the depth of the grooves, as well as their number, are correlated in such a way that the movable transverse wall has essentially the same cross-sectional area when it is positioned in the area of said lands and grooves as when it is positioned in a smooth-walled part of the cartridge.

16. An injection cartridge of the dual-chamber type, comprising:
    a tubular barrel which at its front end is sealed by a closure which may be penetrated by an outlet conduit for a liquid preparation from the cartridge, at its rear end is closed by a piston which may be moved forward, and a movable transverse wall inside said barrel, said movable wall dividing the cartridge into two separate chambers, and a bypass connection between the two chambers, said connection being openable by the displacement of said movable wall to permit a bypass flow of liquid between the two chambers, and characterized in that said connection between the two chambers is arranged as a modification of the interior surface of the wall of the barrel along a determined area, such that said movable wall does not seal completely against said interior wall of the barrel within said area.

17. An injection cartridge according to claim 16, wherein said modification of the interior wall surface of the barrel extends completely around the circumference of said interior wall.

18. An injection cartridge according to claim 16, where said modification of the interior wall surface is arranged as a plurality of lands and grooves in said interior wall.

19. An injection cartridge according to claim 18, wherein the lands extend inward from the nominal interior circumference of the tubular barrel, and the grooves extend outwardly from said nominal circumference.

20. An injection cartridge according to claim 19, wherein the height of the lands and the depth of the grooves, as well as their number, are correlated in such a way that the movable transverse wall has essentially the same cross-sectional area when it is positioned in the area of said lands and grooves as when it is positioned in a smooth-walled part of the cartridge.

* * * * *